US005559097A

United States Patent [19]

Sasser

[11] Patent Number: 5,559,097
[45] Date of Patent: Sep. 24, 1996

[54] USE OF A PREGNANCY SPECIFIC PROTEIN AS AN IMMUNOSUPPRESSIVE

[75] Inventor: R. Garth Sasser, Moscow, Id.

[73] Assignee: Idaho Research Foundation, Inc., Moscow, Id.

[21] Appl. No.: 464,102

[22] Filed: Jan. 12, 1990

[51] Int. Cl.$^6$ ..................................... A61K 38/02
[52] U.S. Cl. ........................ 514/21; 530/399; 530/850; 514/885; 514/12
[58] Field of Search ............................... 424/85.1, 85.4, 424/88, 105; 514/2, 12, 21, 885

[56] References Cited

U.S. PATENT DOCUMENTS 4,554,256  7/1983  Sasser .................................... 436/510
4,705,748  11/1983  Sasser .................................... 436/510

OTHER PUBLICATIONS

Sasser, et al., *J. Reprod Fert.* Suppl 37, 1989, pp. 109–113.
Balton et al., *The Lancet* Mar. 1987, pp. 593–595.
Newton et al., *Am J. Reprod Immunol* 19, 1989, pp. 99–107.
"Identification of Placental Protein as a Immunosuppressive Factor in Human Reproduction", by A. E. Bolton et al., in *The Lancet*, Mar. 14:593–595 (1987).
"Suppression of Interleukin–2–Mediated T–Lymphocyte Blastogenesis by Ovine Uterine Luminal Protein", by E. C. Segerson, Jr. et al., in *Biology of Reproduction*, 38:256–263 (1988).
"Human Pregnancy Serum Inhibits Proliferation of T8–Depleted Cells and their Interleukin-2 Synthesis in Mixed Lymphocyte Cultures", by C. G. Domingo et al., in Journal of Reproductive Immunology, 8:97–110 (1985).
"Inhibition of Lymphocyte Proliferation by Ovine Trophoblast Protein–1 and a High Molecular Weight Glycoprotein Produced by the Peri–Implantation Sheep Conceptus", by G. R. Newton et al., in *American Journal of Reproductive Immunology*, 19:99–107 (1989).
"Suppression of Lymphocyte Activation by a High–Molecular–Weight Glycoprotein Released from Preimplantation Ovine and Porcine Conceptuses", by M. K. Murray et al., in *American Journal of Reproductive Immunology and Microbiology*, 14:38–44 (1987).
"The Influence of Protein Hormones and Conceptus Extracts on Sheep Lymphocyte Transformation Induced *in Vitro*", by L. D. Staples et al., in :125–131 (1983).
"The Influence of Embryonic Tissue Homogenate Infused into the Uterus, on the Life–Span of the Corpus Luteum in the Sheep", by L. E. A. Rowson and R. M. Moor, in J. Reprod. Fert., 13:511–516 (1967).
"Human Pregnancy Serum Inhibits Interleukin–2 Production", by N. S. Nicholas et al., in *Clinical Experimental Immunology*, 58:587–595 (1984).
"Interrelationships Between Uterus and Conceptus to Maintain Corpus Luteum Function in Early Pregnancy: Sheep, Cattle, Pigs and Horses", by W. W. Thatcher, et al., in *J. Admin., Sci.*, 62:25–46 (1986).

"Isolation and Partial Characterization of an Antigen Associated with Pregnancy in the Ewe" by L. D. Staples, in *Biology of Reproduction*, 22:675–685 (1980).
"Suppression of Phytohemagglutinin–Stimulated Lymphocyte Blastogenesis by Ovine Uterine Milk Protein" by E. Segerson, et al., *Biology of Reproduction*, 30:1175–118 (1984).
"Characterization of Immunosuppressive Substances in the Basic Protein Fraction of Uterine Secretions from Pregnant Ewes" by P. J. Hansen, et al., *Biology of Reproduction*, 36:393–403 (1987).
"Effect of Embryo Removal and Intrauterine Infusion of Embryonic Homogenates on the Lifespan of the Bovine Corpus Luteum" by D. L. Northey and L. R. French, Journal of Animal Science, 50:298–302 (1980).
"Trophoblastin, as antiluteolytic protein present in early pregnancy in sheep" by J. Martal, et al., *J. Reprod. Fert.*, 56:63–73 (1979).
"Proteins released by cultured day 15–16 conceptuses prolong luteal maintenance when introduced into the uterine lumen of cyclic ewes" by J. D. Godkin, et al., in J. Reprod. Fert., 71:57–64 (1984).
"Immunosuppressive Effect of Ovine Uterine Secretory Protein upon Lymphocytes in vitro" by E. C. Segerson, in *Biology of Reproduction*, 25:77–84 (1981).
"Characterization of Pregnancy–Specific Protein B in Cattle" by L. D. Staples, in *Biology of Reproduction*, 37:109–113 (1989).
"Ovine Trophoblast Protein 1, and Early Secreted Blastocyst Protein, Binds Specifically to Uterine Endometrium and Affects Protein Synthesis by Godkin", in The Endocrine Society, 114:120–130 (1984).
Segerson et al., CA vol. 101, #2089325, 1984.
Sergerson et al. CA vol. 101 #37126a, 1984.
Roberts et al. CA, vol. 110, #210621u, 1989.
Hansen et al., CA vol. 107, #21779d, 1987.
Niwano et al., Am J Reprod Immunol, 1989, 20, p. 21–26 (Abstract only).
Watson, CA, vol. 112, 196471c, 1990.

Primary Examiner—Garnette D. Draper
Assistant Examiner—L. Spector
Attorney, Agent, or Firm—Rae-Venter & Associates

[57] ABSTRACT

Methods and compositions are provided for maintaining pregnancy and preventing rejection of transplanted tissue. A polypeptide characterized as capable of isolation from conceptus tissue and capable of inhibiting mitogen induced lymphocyte blastogenesis is employed which is introduced into the uterus or systemically.

6 Claims, 2 Drawing Sheets 5,559,097

USE OF A PREGNANCY SPECIFIC PROTEIN AS AN IMMUNOSUPPRESSIVE

TECHNICAL FIELD

The field of this invention concerns compositions and methods relating to immunosuppression in mammals.

BACKGROUND

Circulating lymphocytes respond to the presence of foreign antigens by undergoing blastogenesis. This allows for a major change in cell number and aids in neutralizing the effect of the antigen. It is one way that the immune system meets the challenge of disease or presence of foreign tissue. This response is seen when tissue transplants occur and can result in tissue rejection.

The fetus is also foreign to the host (mother) since it has antigens that are contributed by the paternal genome. Mechanisms preventing maternal rejection of the semiallogenic fetus are not well understood. However, the maternal immune system is fully capable of rejecting paternal antigens expressed by the conceptus and it is well documented in sheep that the uterus is capable of tissue transplant rejection and that the fetus therefore must regulate the immune system in a protective way. Proposed mechanisms include secretion by the fetus of proteinaceous products which act to suppress the immune system.

Ovine Trophoblast Protein-1 (oTP-1) is a conceptus secretory product produced by the ovine conceptus between days 13 and 21 after conception (REF). It is known to have antiluteolytic properties, in particular it prevents functional regression of the corpus luteum, and it maintains progesterone in the circulation and thus maintains pregnancy. The protein does not leave the uterus but instead alters production and/or secretion of prostaglandin F-2, the compound responsible for regresssion of the corpus luteum. oTP-1 has a high degree of homology with the interferon alpha family and possesses antiviral activity. oTP-1 suppresses mitogenesis in lymphocytes stimulated with concanavalin A (CON A), pokeweed mitogen (PWK) or phytohemagglutinin (PHA).

A bovine trophoblast protein (bTP-1) with properties similar to those of oTP-1 also has been identified. It is interferon-like and capable of extending the life-span of the corpus luteum when introduced into the uterus or injected intramuscularly into cattle. It would therefore be of interest to develop compositions and methods of using as a means for maintaining the conceptus and enhancing conception rates and additionally whether they may have immune suppressive properties.

Relevant Literature

Specific proteins secreted from endometrial tissues during early and late pregnancy in the ewe, were found to regulate in vitro lymphoblastogenesis (Staples, *Biol. Reprod.* (1980) 22:675–685; Segerson, *Biol. Reprod.* (1981) 25:77–84; Staples et al., *Placenta* (1983) 4:125–132; Segerson et al., *Biol. Reprod.* (1984) 30:1175–1186; Hansen et al., *Biol. Reprod.* (1987) 36:393–403). Conceptus tissue secretory products, produced when embryos were in the third week of age, suppressed lymphoblastogenesis (Murray et al., *Amer. J. Reprod. Immunol. and Microbiol.* (1987) 14:38–44). The suppressive substance was a high-molecular-weight glycoprotein (molecular weight of >660,000 daltons). Similarly, secretions from the nonpregnant uterus were effective in suppressing lymphoblastogenesis. Suppression was greatest near day 14 of the cycle (Segerson, *Biol. Reprod.* (1981) 25:77–84). Segerson (*Biol. Reprod.* (1988) 38:256–263) showed that uterine luminal protein (UPL) secretions of day 14 of pregnancy in the ewe suppressed blastogenesis of interleukin-2 (IL-2) -dependent T-lymphocytes. Such an effect has also been shown for factors in the sera of pregnant humans (Nicholas et al., *Clin. Exp. Immunol.* (1984) 58:587–595; Domingo et al., *J. Reprod. Immunol.* (1985) 8:97–110). A specific human placenta human placental protein, Placental Protein 14 (pp 14), has been shown to exhibit suppressive lymphoblastogenic activity (Bolton et al., *The Lancet* (1987) 1987:593–595).

Newton et al., (*Am. J. Reprod. Immunol.* (1989) 19:49–67) showed that sheep conceptus secretory proteins contained two immunosuppressive fractions. One fraction was identified as oTP-1 and the other as a high molecular weight glycoprotein. Suppression of elactogenesis by either protein was not reversed by addition of IL-2 when PWM was the mitogen. IL-2 induced proliferation of lymphocytes was suppressed by treatment with HAWG or oTP-1.

The subject of maternal recognition of pregnancy has been reviewed by Thatcher et al. (*J. 15 Anim. Sci.* (62(Suppl 2):25). Early work on this subject showed that ovine embryo homogenate, when infused into the uterus of sheep during the estrous cycle, would extend the life span of corpora luteu (Rowson and Moore, *J. Reprod. Fert.* (1967) 13:511. When infusions were stopped the animals returned to estrus. A similar study was conducted in the cow by Northey and French (*J. Animal Sci.* (1980) 50:298). They concluded that an embryo must be present in the uterus by the 16th day of the estrous cycle if corpora lutea, and thus higher circulating levels of progesterone, are to be maintained beyond a normal cycle length of 21 days. Certain proteins isolated from the ovine conceptus have been shown to extend the length of the estrous cycle. Martal et al. (*J. Reprod. Fertil.* (1979) 56:63) showed this when they infused trophoblastin into the uterus of the ewe during the estrous cycle. Godkin et al. (*J. Reprod. Fert.* (1984) 71:57) have found that ovine trophoblast protein-1 (oTP-1) would do the same thing. The biological response to both of these proteins was similar; the cycle length was extended for varying times from approximately 20 to more than 45 days in individual animals. The latter protein is not secreted by the conceptus after 24 days of age.

SUMMARY OF THE INVENTION

Composition and methods for protecting the fetus from immunorejection by the mother as well as methods for suppressing rejection of other "foreign" tissue are provided. The method involves using secretory proteinaceous products produced by the conceptus following implantation and during pregnancy and introducing them into the uterus at the time of conception to enhance the pregnancy rate or during pregnancy, particularly when spontaneous abortion is threatened to prevent fetal rejection. The polypeptides may be introduced systemically to suppress the immune system, for example following tissue transplantation.

DESCRIPTION OF THE SPECIFIC EMBODIMENTS

Figure 1:
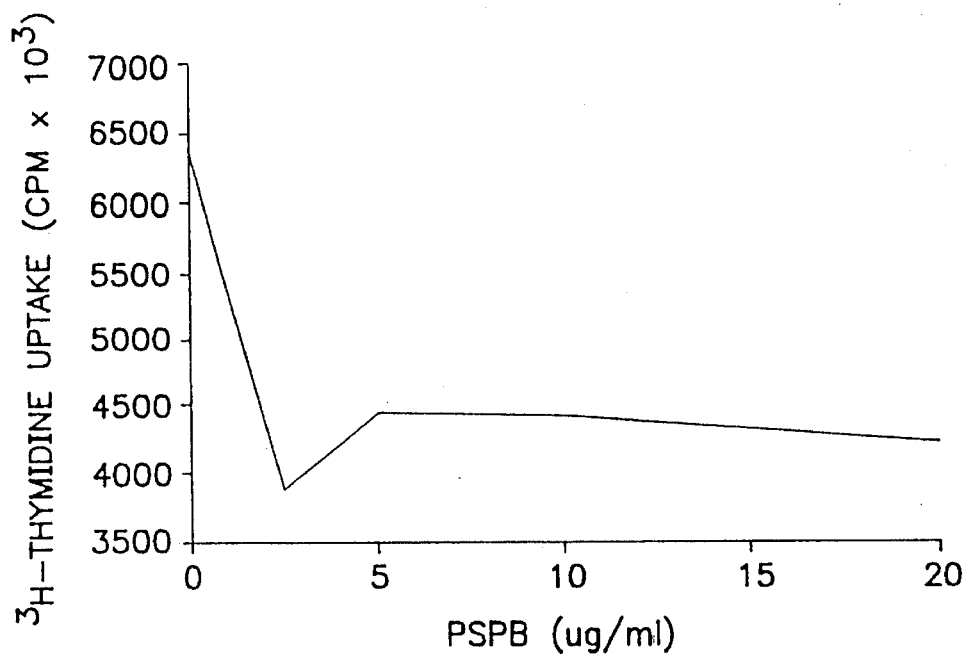
FIG. 1 shows the effect of PSPB on the spontaneous proliferation of lymphocytes in the absence of mitogens.

Methods and compositions are provided for immunosuppression particularly as related to maintenance of pregnancy in mammals, particularly in ruminants, more particularly in domestic animals. The method comprises introducing into the uterus of a host animal following fertiliztion or during pregnancy of trophoblast-secreted proteins to immunosuppress the host, particularly to prevent spontaneous abortion, rejection of a foreign embryo, or a tissue transplant or to enhance pregnancy rate. For general immunosuppression of the host, the trophoblast secreted protein may be administered systemically.

The polypeptides of the subject invention are characterized as capable of isolation from conceptus tissue and capable of inhibiting mitogen-induced blastogenesis. The polypeptides of interest may be isolated from a physiological fluid, such as serum, milk, tears, saliva, placental fluids and urine, of a pregnant host, or preferably from mammalian, particularly ruminant conceptus tissue, such as placental tissue from embryos of at least about 12, usually at least about 14 days past fertilization. A polypeptide of particular interest is Pregnancy Specific Protein B (PSPB) which is present in serum of pregnant cows and is detectable in some animals at 15 days, more usually from 24 to 282 (parturition) days of gestation. A protein which crossreacts with antisera to PSPB is also present in sera from pregnant white-tailed deer and mule deer, elk and bighorn sheep, mountain goats and other domestic or wild ruminants.

PSPB can be extracted from tissues and fluids within which it is located. Placental tissue is a good source because it has a high concentration of PSPB. Placenta of all ruminants is likely to have this protein; it is not restricted to cow or sheep placenta. Giant binucleate cells of the trophoblast also produce this protein (Reimers et al., *Biol. Reprod.* (Suppl. 2) 32:65, 1985). PSPB may also be obtained by culturing placental tissue or binucleate cells and extracting it from the culture medium. Yield is low compared to that of placental extraction. PSPB can be isolated from endometrium of pregnant cows or early postpartum cows (but not other cows). It also can be extracted from fluids of the placenta. It is in blood and can be extracted from there. PSPB is also present in semen of bulls. SPI, human chorionic gonadotropin, human placental lactogen and placental protein 5 (PP5), which are all placental proteins also have been found in semen (Chard, Pregnancy Proteins. Academic Press Australia. 1982). It is also possible to locate the gene encoding PSPB and place it into a cell system, either bacterial, yeast or mammalian cells, and produce recombinant PSPB using mehtods known to those skilled in the art.

The polypeptide of interest may be isolated from conceptus tissue in accordance with the following procedure. Conceptus tissue such as placental membranes or cotelydonary tissue is minced and homogenized, the solids separated and the supernatant collected. Desirably, the temperature is maintained at or below about 10° C., preferably below about 5° C. To the supernatant, generally at a temperature below about 5° C., usually between about 0°–5° C. is added ammomium sulfate and the fraction precipitating usually between about 45 and 75% saturation with ammomium sulfate isolated. A precipitate is dialized against an appropriate buffer, for example, Tris HCl at a physiological pH, for example about pH 6.5–9 in a dialysis tube with an exclusion limit appropriate for the polypeptide to be isolated. Dialysis is carried out for about 48 hours against high volumes of buffer usually at between about 0°–5° C. The dialysate is then concentrated and chromatographed using a resin suitable for separation of the polypeptide of interest.

Where the polypeptide of interest is PSPB, for chromatography, conveniently the resin is a cation exchange resin such as diethylaminoethyl cellulose (DEAE cellulose). Elution is performed employing as the eluant a buffered aqueous solution at about physiologic pH, for example about pH 6–9, more usually pH 7.5, followed by a linear or stepwise salt gradient. Fractions are isolated and monitored by absorption at 280 nm. Fractions containing the polypeptide of interest can be determined by immunoassay if antibodies are available, or by bioassay using, for example the suppression of mitogen induced lymphoblastogenesis. If necessary, the polypeptide of interest may be further purified using techniques known to those skilled in the art such as gel filtration, affinity, chromatography, electrofocusing, reverse phase high pressure liquid chromatography (HPLC) and the like. Additionally, the polypeptide of interest may be concentrated by ultra filtration or other methods known to those skilled in the art.

The polypeptides of interest have a variety of uses. The polypeptides can be introduced into the uterus so as to act as stabilizing immunosuppressive factors at low concentrations and lessor immunochallenge in early pregnancy and as an immunostimulator at higher concentrations and greater immunochallenge, by the fetus, in late pregnancy. In the latter case, they could aid in induction of parturition through lysis or otherwise induce breakdown of the placentoma. The means of administration is not important except that it should be one which does not compromise the pregnancy if administration is to maintain pregnancy. The polypeptides of interest thus may act as immunosuppressive substances which aid embryo survival. Injection, additionally, could aid in maintenance of pregnancy by other means other than immunosuppression, such as retained progesterone secretion by the corpus luteum or stimulation of other pregnancy related factors.

Tissue transplantation occurs routinely in medicine. Organ transplants are often rejected by the host. Drugs that suppress the immune system are used routinely to prevent tissue rejection. Systemic introduction in an amount sufficient to suppress the immune system of the host of substances produced by placental tissue, including PSPB may thus be used in aiding maintenance of foreign tissue in transplant recipients. Placement of an immunosuppressant amount of the polypeptides of interest in resorbable sutures or packing around tissues may protect an organ in a manner similar to that by which conceptus-produced immunosuppressants protect the fetus and placenta.

Liposomes and other substances are used to target drugs by way of the circulation to specific tissues. The liposome contains agents that cause binding to the specific tissue and the drug is released slowly at the target site. Thus, an immunosupressor such as PSPB in an amount sufficient to provide for immunosppression of the host could be used to protect transplanted tissue from immunorejection by incorporation into a liposome. Linking of targeting molecules such as antibodies to liposomes is well known to those skilled in the art. See for example Heath et. al. *Proc. National Acad. Sci.* USA (1983) 80:1377–1381 and Leserman et. al. *Nature* (1981) 293:226–228. For the preparation of liopsomes see for example Szoka and Papahadjopoulos, *Proc. National Acad. Sci.* USA (1978) 75:4914–4198 and Szoka et. al. *Biochem. et Biophys. Acta* (1980) 601:559–571.

Placental immunosuppressive substances of a species are required to prevent immunological rejection of the conceptus. Transplantation of an embryo of one species into the uterus of another generally results in abortion of the embryo, for example, goat embryos placed into the uterus of sheep do not develop to term. Sheep-goat chimeric embryos, which have tissues derived from both the sheep and goat genome are known to survive to term in the sheep uterus (Polzin et al., *J. Anim. Sci.* (1987) 65:325). There is a case of a goat being born to a sheep. This animal, as an embryo, was the result of artificially induced chimerism. An inner cell mass of a goat embryo was placed with that of a sheep and then the whole cell mass was transplanted into the uterus of a sheep. It is speculated that the goat fetus survived because the placenta was that of a sheep and the maternal system did not reject it. The genes for immunosuppressive substances such as PSPB could be cloned into the genome of goats or other species to help maintain the pregnancy of the foreign embryo in the uterus of the sheep, cow or other species. This could be of value in helping to extend the number of animals of one species (perhaps endangered species) by transfer to the uterus of domestic animal such as the cow.

It is also possible that the placement of an extra gene into the genome of the same species will result in a greater presence of specific (e.g., PSPB) placental immunosuppressors and increase the conception rate with these individuals of the species of interest.

PSPB has several other potential uses as an immunosuppressant, including the following. It may be injected where it may have a pharmacological effect including effects at the uterine level and the ovarian level. For example, it is possible that intramuscular or intravenous injection of pharmacological doses of PSPB can be used to suppress the immune system and maintain a pregnancy. This would result in increased embryo survival due to increased immunoprotection of the embryo. PSPB therefore may be administered in a manner similar to that used with other embryonic proteins as follows. Ovine and bovine trophoblast protein-1 (oTP-1 or bTP1) have been shown to be interferons (Imakawa, *Nature* (London) 330.337–339, 1987) and both these proteins and interferon suppressed lymphocycte blastogenesis Just has been shown for PSPB. In addition, interferon infusion into the uterus mimiced the effect of oTP-1 or bTP-1 in that it lengthens the estrous cycle, a necessary event for embryo maintenance. Intrauterine dosage is not feasible routinely when there is a pregnancy. Another route of treatment was desired and was tested by Plante et al., (*J. Dairy Sco.* 71:1859–1865. 1989) in cows and by Chalue-Francis et al. (*Biol. Reprod.* (Suppl. 1) 40:85, 1989) in sheep. These researchers gave intramuscular injections of the inteferons. In the sheep, recombinant bovine interferon-alphaI-7 (CIBA-GEIGY, Ltd.), given twice daily at 2 mg/dose did not extend the luteal phase of the estrous cycle. It did increase pregnancy rate from 58% in placebo treated ewes to 79% in interferon treated ewes. In the cow, this same interferon preparation lengthened the estrous cycle. An effect on pregnancy rate was not tested. These pharmacological doses likely have an effect by changing protaglandin F-2 alpha (and/or other substances) secretion from the uterine endometrium resulting in luteal maintenance. Although similar doses of oTP-1 or bTP-1 have not been given due to unavailable quantities, it is presumed that they too would have this effect.

It is also possible that these proteins, since they have been shown to be immunosuppressive, provide immunoprotection to the embryo. Similarly, PSPB could provide protection to embryos and increase pregnancy rates in cattle and sheep and perhaps other mammals.

At the ovarian level, Fairchild and Pate (*Biol. Reprod.* 40:453–457, 1989) found that the major histocompatibility complex (MHC) antigens (class I and class II) were present on cells of the corpus luteum of the ovary in the cow. The concentration of these antigens increased as time of luteolysis (reulting in luteal regression and start of a new reproduction cycle) neared. It has been proposed that expression of MHC antigens results in lymphocyte infiltration and this in turn may cause destruction of luteal cells leading to luteolysis and the end of the reproductive cycle. Luteinizing hormone, a stimulator of luteal cell function, reduced the expression of MHC antigens on these cells. When lymphocytes were attracted to the corpus luteum, they released interferon gamma which caused further induction of the MHC and possible resultant luteolysis. Certain agents, i.e. norepinephrine (Frohman et al., 1988, *Proc Natl Acad Sci* USA 85:1292–1296) inhibited induction of MHC antigens by interferon-gamma. An immunosuppressive role of PSPB, of inhibiting lymphocyte blastogenesis may be to suppress this lymphocyte-induced rejection of the corpus luteum. The time of luteolysis after the day of heat for a normally cycling cow is about the same time that PSPB initially enters the circulation of the pregnant cow (Sasser, et al., *Biol Reprod.* 35:936–942, 1986). This is near the end of a normal estrous cycle. This prevention of luteolysis would provide for maintenance of pregnancy.

Other potential uses of PSPB include antiviral activity. Antiviral activity of high specific activity is a classic characteristic of interferonalpha. Ovine trophoblast protein-1 (oTP-1) is closely related to this type of interferon. In humans, significant levels of interferon-alpha activity were present in fetal blood, organs, placenta, amniotic fluid and dedidua in the absence of an inducer (Chard et al., *Brit. J. Obstet. Gynaecol.* 93:1145–1149, 1986). Pontzen et al., (*Biochem Biophys. Res. Communic.* 152:801–807, 1988) showed that oTP-1 also has high antiviral activity. Other conceptus products involved in immunosuppressive activity, including PSPB, could play a role in such an interferon-related action. It may be that the role of PSPB is not as an interferon-alpha or suppressor of such, but as another type of interferon such as interferon-gamma or a suppressor of such which is involved in preventing induction of the major histocompatibility complex antigens as discussed above.

PSPB may also find use as a tumor marker. Placental proteins and pregnancy-related proteins have been used as indicators of malignancies in humans. For example, pregnancy-specific beta-1 glycoprotein (SP1) is synthesized by the placental trophoblast, trophoblastic tumors (Bohn and Sedlacek, Arch. Gynakol. 220:104, 1985; Tatarinow et al., *Nature* 260:263, 1976; Heikinheimo et al., *Acta Microbiol* 89:139, 1981) and certain types of nontrophoblastic tumors in vitro (Rosen et al., *Amer. J. Obstet. Gynecol* 134:734, 1979; Azer et al., *J. Clin. Endocrinol. Metab.* 50:234, 1980; Heikinheimo et al., *Br. J. Cancer* 43:654, 1981). Circulating SP1 may indicate presence of tumors in the non-prgnant individual. A review of this subject is presented by M. Seppala and E. Rutanen (*In Pregnancy Proteins.* 1982. *Acad. Press*, Australia). PSPB may be antigenically related to certain types of human or other mammalian tumor proteins and may find use as a means for identifying presence of tumors.

SP1 may also find use as a threatened-abortion marker (low levels of PSPB may indicate impending abortion). Ho and Jones (*Amer. J. Obstet. Gynecol.* 138:253, 1980) found that abnormally low SP1 (a placental protein of the human) concentration in serum was an indicator of threatened abortion and in some cases ectopic pregnancy. This subject is briefly reviewed by Warren et al. (*Pregnancy Proteins*. p. 241. Acad. Press, Austr., 1982). Low levels of PSPB are present in the circulation at a set time of pregnancy (usually before 70 days of gestation) and resorption (embryonic mortality) of the conceptus ensued (Humblot et al., Theriogenology (1988) 30:257–267.

PSPB may also find use as a means to induce sterility or use as a contraceptive. There is considerable interplay between the newly present conceptus and the maternal system. Several substances are produced by the conceptus which regulated its own survival. Ovine and bovine trophoblast protein-1 alter uterine function thereby preventing protaglandin-induced luteolysis. The finding of early pregnancy factor (EPF) by Morton et al., (*Nature*, Lond. 249:459–560, 1974; *Proc. R. Soc. Brit*.193,413–419) showed that a signal released within hours of conception is perceived by the maternal system. EPF is released from the ovary and is known to initiate production of suppresor factors for lymphocyctes, which in turn, suppress certain immunological responses such as cell-mediated hypersensitivity reactions (Rolfe et al., *J. Clin. Expt. Immunol.* 73:219–225, 1988). Athansas-Platsis et al. (*J. Reprod. Fert.* 87:495–502) conducted a study to see if this immunosuppressive was necessary for maintenance of pregnancy. They passively immunized mice with both polyclonal and monoclonal antibodies to EPF shortly after animals were bred and pregnancy success was monitored. It was found that less than half the mice maintained their pregnancies.

PSPB, a immunosuppressor, may also be required for maintenance of pregnancy. Neutralization of PSPB by active (immunizing against PSPB) or passive (giving exogenous antibodies) antibody therapy may be useful as a means to sterilize animals. Sterilization is of importance to livestock producers in that cull females are of more value if they can be guaranteed non-pregnant when sold to feedlots. Immunization against PSPB may be a way to induce this sterility in cattle, sheep and perhaps other meals. This treatment could also find use as a contraceptive.

The following examples are offered by way of illustration and not by way of limitation.

EXPERIMENTAL

RIA and iodination and antibody titration bPSPB was radio-iodinated and RIAs were performed according to the methods of Sasser et al. *Biol. of Reprod.* (1986) 38:936–942. Titers of antisera were determined by a binding test. Binding of labeled PSPB (45,000 cpm) to antisera were determined by addition of various dilutions of antisera, assay buffer, and labeled PSPB followed by incubation overnight. Sheep antiserum to rabbit gamma globulin was then added (200 microliters, diluted 1:8) and incubated for 48 hours. Samples were centrifuged and the precipitate was counted.

Production of antibodies

Proteins from the 70 mM NaCl cut in the DEAE extraction sequence were separated by SDS-PAGE as previously described except that a single, 140 mm-wide well was used. The gels were stained with Coomassie blue and protein bands of interest at 64, 70, and 90 kD were excised and equilibrated for 2 hours in sodium phosphate buffered saline pH 7.0 (PBS). The 64, 70, and 78 kD bands contained approximately 75, 75, and 125 µg of protein, respectively. Each gel slice was homogenized in 1 ml PBS with a Tekmar (Cincinnati, OH) SDT1810 homogenizer at 100% speed for 30 seconds. One ml of Freund's complete adjuvant was added to the gel mixture and thoroughly emulsified. The emulsions were injected intradermally at approximately 35 sites along the backs of 2 kg, male, New Zealand White rabbits. At this time 0.5 ml of human diphtheria-tetanus vaccine (DT) was injected intramuscularly. Similarly, rabbits received booster immunization at 3, 6, and 9 weeks after the initial injection except that Freun's incomplete adjuvant was used and no DT was administered.

Blood was collected weekly from 3–9 weeks after the initial injection from the medial ear vein. Serum was obtained and stored at −20° C. Titers were determined in a binding assay with $^{125}$I-bPSPB and by double radial immunodiffusion (Ouchterlony and Nilsson, In: *Handbook of Experimental Immunology* 3rd Ed. (D. M. Wies, ed.) (1978) Blackwell Scientific Publications, London) against supernatant from bovine placental homgenate.

EXAMPLE I

Preparation of PSPB from tissue

PSPB was obtained from cotyledonary tissue of cow placenta. Cotyledons (400 g) were placed in a beaker containing 500 ml of cold 10 mM Tris-HCl at pH 7.5 and 75 g of coarse silica sand. This was stirred on a magnetic stirrer at 4° C. until the cotyledons appeared opaque (about one hour). This disrupted cells from the surface microvilli of the cotyledons. The cotyledons were removed and the fluid was centrifuged at 1800 g for 10 min and the supernatant was subjected to an ammonium sulfate precipitation between 45 and 75% saturation. The precipitate was dissolved in 1 mM phenyl methyl sulfonyl fluoride, 0.2% NAN3, 10 mM TRIS-HCl, pH 8.5, and dialyzed (3500 molecular weight cutoff) against 20 volumes of 1 mM Tris-HCl, pH 8.5. The pH of the dialysate was then adjusted to 3.6 with 1M HCl and centrifuged at 1800 g for 10 min. The pH of the supernatant was immediately adjusted to 8.5 with 1M NaOH. The supernatant was then dialyzed as before.

The extract was loaded onto diethyaminoethyl (DEAE) cellulose resin which had been equilibrated in a 10 mM NaCl solution at pH 7.5. Loading rate was 5 mg protein per ml of DEAE. The DEAE was washed in a Buchner funnel with TRIS-HCl, pH 7.5, containing 30 mM NaC1. It was the washed successively with TRIS-HCl, pH 7.5 containing 50 mM and then 70 mM NaCl and the effluent was saved. The effluent was concentrated by ultrafiltration (30,000 MW cutoff) and sterile filtered for storage at 0°–4° C.

Immunoaffinity gel was prepared by precipitation of IgG from rabbit anti-bPSPB antisera (Sasser et al., 1986) with addition of $(NH_4)_2SO_4$ to 30% saturaton at 4 C. The antisera was centrifuged at 1000 ×g for 15 min then resuspended in 5 mM $H_3BO_3$, 1.25 MM $NA_2B_4O_7$ saline (BBS), pH 8. The IgG fraction was precipitated twice more then dialyzed against several changes of distilled water and finally against 100 mM HEPES, pH 7.5.

The IgG fraction was added to Affi-Gel 10 at a rate of 10 mg protein/ml gel and shaken at 4 C for 4 h. The gel was extensively washed with BBS-0.1% Triton X-100, then 8M urea and finally with BBS-1.0% $NAN_3$.

After coupling the IgG to the affinity gel, 10 µl of gel were shaken with $^{125}$I-bpSPB (Sasser et al., *Biol. Reprod.* (1986)

35:936) for 1 h then washed with BBS. One ml of 50% ethylene glycol, BBS-0.1% Triton X-100, 500 mM Glycine-HCl pH 2.5, 150 mM NH$_4$OH, 8M Urea, 2.0M KSCN, or 2.5M KI was added to the gel and shaken for 3 min. The gel and the supernatant were counted separately for 1 min to determine the optimum antigen releasing conditions.

The affinity gel was shaken gently with concentrate from the DEAE extraction step for 1 h at ambient temperature. The mixture was placed in a Buchner funnel, aspirated, and washed with 7×gel volumes of BBS-0.1% Triton X-100 then with 5×gel volumes of 2.5M KI. The effluent was concentrated and desalted by ultrafiltration (30,000 MW cutoff).

The extraction scheme yield a nearly pure product with a single major band on SDS-PAGE at a Mr of 64,000 and two additional minor bands at 70,000 and 78,000.

In the analyses above, the standards were run under non-denaturing conditions but the samples were run under denaturing conditions. When the standards and samples were run under denaturing conditions by reduction with 2-mercapto ethanol, the mobility of the standards changed downward with respect to the standards run under non-denaturing conditions. Accordingly, the molecular weight of the proteins being determined also changed downward even though they did not change in mobility or position on the gel. Using the denatured standards, the molecular weights changed to 64, 70 and 78 kD, respectively, instead of 78, 85 and 90 kD.

EXAMPLE II

Isolation of PSBB from Cultured Tissue

Cotyledons were aseptically removed from 90–110 day placentas and placed in Hanks' balanced salt solution with 30 mg penicillin and 500 mg streptomycin/l for about 30 minutes. Approximately 5 cotyledons were placed in 250 ml Falcon 3024 tissue culture flasks along with 30 ml of M199 media containing 30 mg penicillin and 500 mg streptomycin/l. The cotyledons were incubated at 37° C. with a 5% CO$_2$, 95% air atmosphere for 3 days. The medium was being changed daily. The conditioned medium was collected and dialyzed (12,000 MW cutoff) against 100 volumes of 1 mM Tris-HCl, pH 8 and stored at −20° C.

Proteins were separated by discontinuous sodium dodecyl sulfate-polyacrylamide gel electrophoresis (SDS-PAGE) (Laemmli, et al., Nature (1970) 227:680–685 with 4% T stacking gels and 8 to 13% T linear gradient separating gels. Sample buffer did or did not contain b -mercaptoethanol. Gels were run at a constant 20 mA until proteins entered the separating gel when the current was increased to a constant 30 mA. Proteins were stained with silver (Merrill et al., Sci. (1981) 211(27):1437–1438), 25% Coomassie blue R-250, Stains-All (Green et al., Anal. Biochem. (1974) 65:66–72) or periodic acid-alcian blue (Wardi et al., Anal. Biochem. (1972) 49:607–609) or transferred to nitrocellulose and probed with rabbit anti-bPSB antisera (Sasser et al., Biol. of Reprod. (1986) 35:936–942) at a dilution of 1:300 or 1:1000 or a 1:30 dilution of anti-bPSPB antisera which had been obtained from rabbits injected with various sections of SDS-PAGE gels after cotyledonary extracted bPSPB had been electrophoresed into them. Bound rabbit IgG was detected with goat anti-rabbit IgG coupled to alkaline phosphatase and diluted to 1:1000. Nitro-blue tetrazolium and 5-bromo, 4-chloro indolyl phosphate were used as substrates (Blake et al.,Anal. Biochem. (1983) 136:175–179).

Isoelectric focusing was carried out in 2×150 mm tubes with 3.5% pH 3–10 and 1.7% pH 2.5–5 ampholytes in 3.5% T and 8M urea at 400 V for 12–16 h. For the last 1 h the potential was increased to 800 V. The pH gradient was measured by colored acetylated cytochrome markers and by slicing the gel into 5 mm slices and segments and eluting the ampholytes. Isoelectric focusing gels were overlayed onto SDS-PAGE slab gels and the two were sealed together with 1% agarose (O'Farrell et al., (1975) J. Biol. Chem. 250:4007). The second dimension of electrophoresis was performed on 4% T stacking and 8–13% T linear gradient separating gels.

Peptide mapping was performed on 4% T stacking and 10 to 18% linear gradient separating gels. For peptide mapping, the agarose stacking gel was overlayed first with protein sample and then with either 45 µg Staphlococous aureus V8 protease (Lam et al., Anal. Biochem. (1980) 108:220–226) or 60 µg papain in sample buffer (Laemmli et al., Nature (1970) 227:680–685) without beta-mercaptoethanol and the gel was electrophoresed until bromphenol blue from the stacking gel began to enter the separating gel. The gel was removed from the electrophoresis buffer and incubated at 37° C. for 1 h before electrophoresis was resumed. Proteins separated by 2-D gels were stained with silver or transferred to nitrocellulose for a Western blot visualization.

Autoradiograms of Western blots with $^{125}$I labelled proteins were made by exposing Kodak X-AR film to the nitrocellulose for 3 to 10 days at either −70 °C. or ambient temperature. A) and phosphorylase B (97 kD). K and R were calculated according to Siegel and Monty (1965).

Media from cultured cotyledons contained five proteins when separated by SDS-PAGE that were also detectable by anti PSPB (Sasser et al. (1986) supra antibody) on a Western blot. The major immunoreactive band had an estimated MW of 64 kD. Minor immunoreactive bands had estimated MW's of 78, 70, 50, or 37 kD. Some preparations of media also contained a faintly reactive sixth band with an estimated MW of 35 kD. The 50 kD protein was not BSA since BSA did not contain any immunoreactive bands on a Western blot.

Two dimensional electrophoresis showed that the preparation contained seven isoelectric variants of the 64 kD band of bPSPB with pI's between 4.1 and 4.3. These variants we're also secreted into cell culture media by cotyledons from placenta of 90–110 days, suggesting that these variants are not artifacts from the extraction sequence. Two variants with pI's of approximately 4.2 were the most abundant variants in both preparations and in the culture media.

Peptide maps of these variants showed similar digestion products. This would indicate that all variants are charge isomers of bPSPB and not different proteins with similar molecular weights and pI's. All radioiodinated peptide sequences produced by papain digestion were also still recognizable by the original antibody used in pregnancy detection (Sasser et al., Biol. of Reprod. (1986) 35:936–942. S. Aureus protease digestion produced more peptides than did digestion by papain. All peptides detectable by radioiodination were also detectable by antibody Sasser et. al. (1986) supra except the largest peptide with a Mr of approximately 60,000 Regression analysis of $K_{av}$ versus MW for the five standards separated by gel filtration yielded a equation of: $K_{av}$-0.631×log MW+3.221 (R-square=0.9420). Using this equation the MW of bPSPB was 64 kD. Regression analysis of $(-\log (K_{bv}))^{1/2}$ versus $R^3$ gave an equation of $(-\log (K_{bv}))^{1/2}$−0.0165×$R_s$+0.217 (R-square - 0.9924). Stoke's radius for bPSPB was calculated to be 38.4 A.

Titers of antisera produced against the 64 kD, 70 kD and 78 kD proteins were highest at 36.1%, 12.3% and 21.9% $^{125}$I-bPSPB bound, respectively, at a 1:100 dilution of antisera in the binding check. Titers determined by radial immunodiffusion were one for all antisera.

EXAMPLE III

PSPB Inhibition of Mitogen-Induced Lymphocyte Blastogenesis

Lymphocyte Isolation

Six Hereford steers were used as blood lymphocyte donors. These animals were free of disease and physical impairments. They were fed and watered while free in a drylot corral. Blood was collected under sterile conditions from the jugular vein into tubes containing 10% sodium citrate (0.5 ml/10 ml blood). Lymphocytes were harvested from blood by the Ficoll-Paque technique after methods described by Segerson (*Biol. Reprod.* (1981) 25:77) and Toelker et al. (1988). Briefly, gradient centrifugation using Histopaque-1083 (Sigma Chemical Co., St. Louis) was used. Contaminating red blood cells were lysed with addition of 20 ml of pyrogenfree, distilled water followed in 30 seconds with 10 ml of 2.7% (wt/vol) sterile saline to return to isotonicity. Lymphocytes were washed and resuspended in HEPES (N-2-hydroxyethylpiperazine-N'-2-ethanesulfonic acid)-buffered RPMI-1640 (Roswell Park Memorial Institute) (Sigma) supplemented with 100 units of penicillin/ml, 10 micrograms streptomycin sulfate/ml, 10% heat-inactivated (56° C. for 20 minutes) fetal calf serum, and $5 \times 10^{-5}$ M 2-mercaptoethanol. Cells were counted in a Coulter Counter (Model ZBI, Coulter Electronics, Hialeah, NY) and the percent lymphocytes was determined using a Wright-stained smear. Cell viability was determined by Trypan blue exclusion. Percent viability and lymphocytes exceeded 95%. Final concentrations of viable lymphocytes was adjusted to $2.5 \times 10^6$/ml for use in the lymphocyte transformation assay.

3. Lymphocyte Transformation Assay:

This assay was conducted in 96 well mirotiter plates. Eighty microliters of cell suspension was pipetted into each well ($2 \times 10^5$ cells). Then, 100 microliters of mitogen of varying concentrations and 20 microliters of PSPB of varying concentrations were added. Plates were incubated at 37° C. in a humidified atmosphere of 95% air, 5% $CO_2$. After 48 hours, 1 microcurie (20 microliter) of 3H-thymidine was added and plates were incubated for another 24 hours. Cells were then harvested from the wells by aspirations onto microfiber filters. Filters were dried and counted in a liquid scintillation spectrometer to determine rate of incorporation of labeled thymidine into cells. Mean counts per minute of each triplicate were used for statistical analyses.

4. Experimental Design:

The objective of this study was to determine if PSPB would suppress mitogen-induced lymphocyte blastogenesis. The experimental design was a four by five factorial with four concentrations of mitogen and five concentrations of PSPB. Three mitogens were tested. Pokeweek mitogen (PWM) and concanavalin A (Con A) were used at a final concentration of 0, 5, 10, and 20 micrograms/ml and phytohemagglutinin (PHA) was used at 0, 15, 30 and 60 micrograms/ml. Several doses of mitogen were used to assure that optimal stimulation of lymphocytes occurred. PSPB was added at a final concentration of 0, 2.5, 5, 10 and 20 micrograms/ml. As a control to test if protein added to media suppressed blastogenesis, bovine serum albumin (BSA) was added to wells instead of PSPB at doses of 5 and 20 micrograms/ml. Three replicate wells were incubated for each portion of the factorial design.

5. Results:

Bovine serum albumin (BSA) did not alter the rate of incorporation of tritiated thymidine into lymphocytes. Thus, the addition of protein to the medium was not a problem in this study. Table 1 shows the results from the lymphocyte transformation assay. These data are also shown graphically in FIGS. 1 through 4. The statistical comparisons are for a response to a given dose compared to the response at zero dose of PSPB.

TABLE 1

3H-Thymidine incorporation (cpm) into lymphocytes in the presence of varying doses of mitogen and PSPB.

| MITOGEN | Dose, PSPB (UG/ML) | MITOGEN DOSE | | | |
|---|---|---|---|---|---|
| | | 1 | 2 | 3 | 4 |
| PWM | 0 | 6340 | 196385 | 193669 | 181738 |
| | 2.5 | 3917 | 186896 | 187127 | 178232 |
| | 5.0 | 4443 | 194105 | 179358 | 171126 |
| | 10.0 | 4438 | 166034 | 167851 | 160163 |
| | 20.0 | 4266 | 156726 | 154868 | 159148 |
| Con A | 0 | 6340 | 199703 | 245326 | 256735 |
| | 2.5 | 3917 | 197727 | 235191 | 256545 |
| | 5.0 | 4443 | 237977 | 264102 | 262275 |
| | 10.0 | 4438 | 192728 | 232055 | 249521 |
| | 20.0 | 4266 | 182899 | 215358 | 232147 |
| PHA | 0 | 6340 | 193049 | 201157 | 131782 |
| | 2.5 | 3917 | 152952 | 207734 | 156859 |
| | 5.0 | 4443 | 89240 | 195291 | 194613 |
| | 10.0 | 4438 | 33765 | 74477 | 218038 |
| | 20.0 | 4266 | 12081 | 22543 | 215537 |

The 1 through 4 doses of mitogen were 0, 5, 10, and 20 μg/ml respectfully for Con A and PWM and was 0, 15, 30 and 60 g/ml.

When no mitogen was added to the incubate, incorporation of label to the incubate was minimal and PSPB further reduced this at all doses tested. This suggests that cell division of resting lymphocytes would be inhibited by PSPB. The effect of PSPB on mitogenesis when no mitogen was added to the incubate is shown in FIG. 1.

Figure 2:
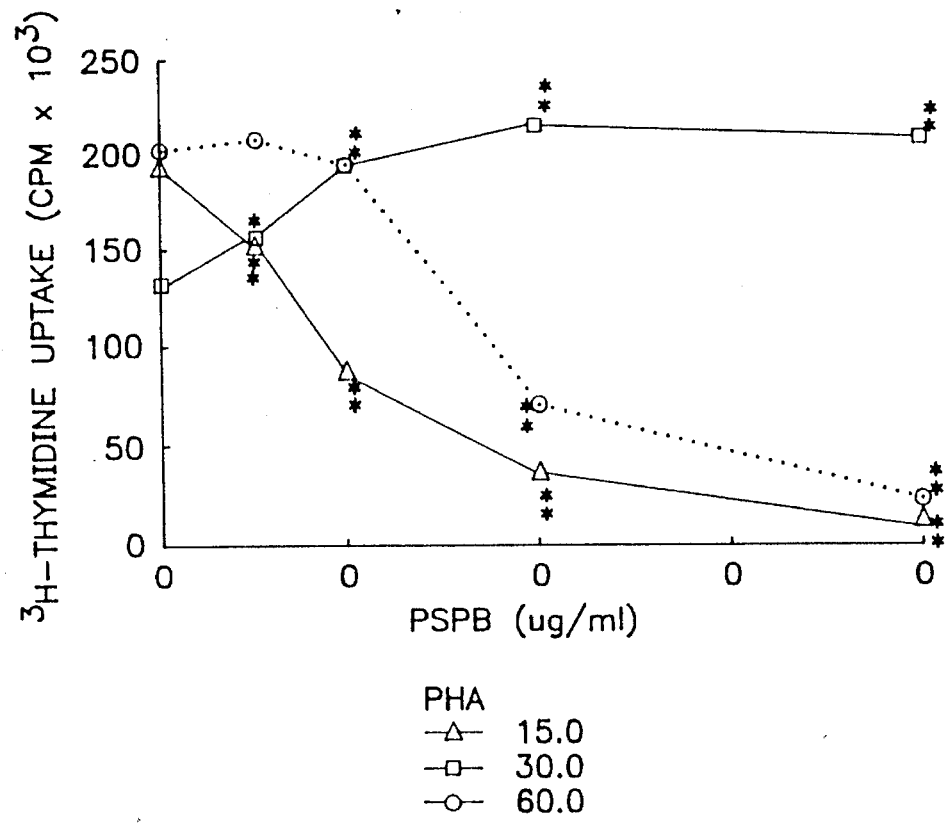
FIG. 2 shows PSPB suppression of phytohemagglutinin (PHA)-induced lymphocyte proliferation (Pooled standard error =2329 cpm; for each line, starred points denote a significant difference from O PSPB (* $P<0.1$, ** $P<0.01$)).

PSPB reduced uptake of label by lymphocytes. The protein was effective at very low doses compared to the response seen with other mitogens. At the two lower doses of mitogen there was significant reduction (p<0.01) of blastogenesis at all but two doses of PSPB at the intermediate mitogen dose doses of PSPB. The response for the PHA mitogen is shown in FIG. 2.

At the highest dose of mitogen, label uptake was lowest compared to other doses when no PSPB was added to the incubate. This suggests that the dose for optimum stimulation of lymphocytes was exceeded. PSPB, on the other hand, caused the opposite effect at this high dose. It increased blastogenesis (p<0.01 in all but the 2.5 microgram/ml dose when it was p<0.05). This suggests that the protein relieved the inhibitory effect of the higher mitogen dose and allowed cells to behave optimally. It is possible that doses of PSPB above 20 would eventually inhibit at this dose as well. This is suggested by the response at the intermediate dose of mitogen. Here the first two doses of PSPB did not reduce the response but then it occurred at subsequent doses.

Figure 3:
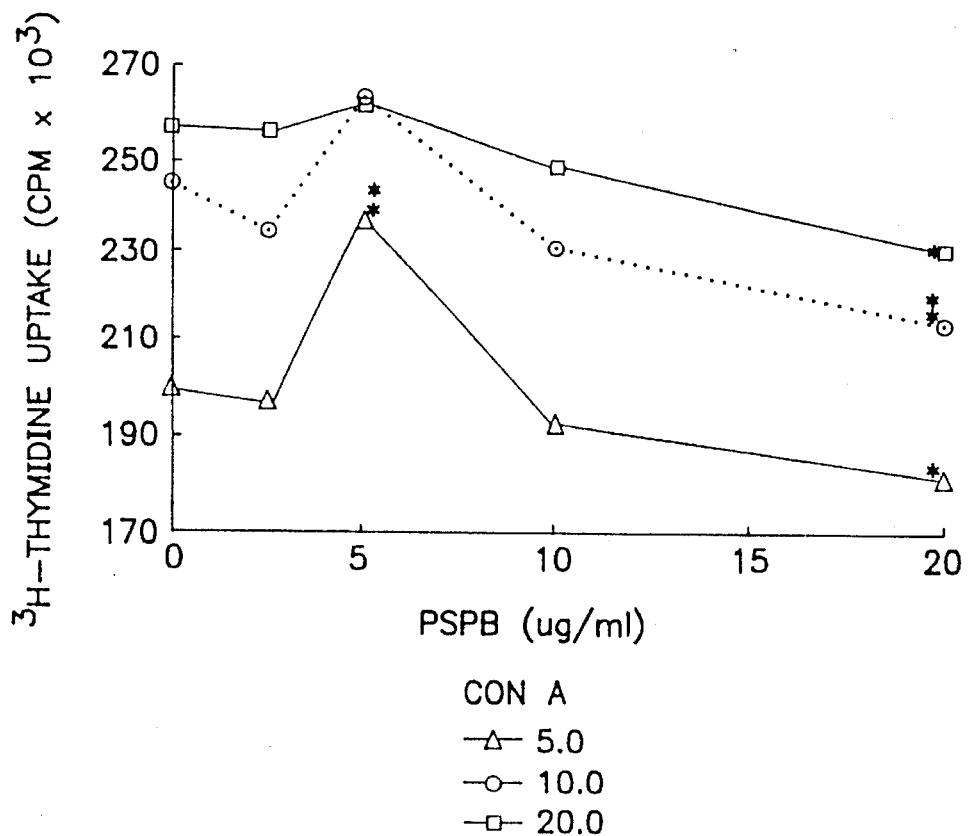
FIG. 3 shows PSPB suppression of concanavalin A (Con A)-induced lymphocyte proliferation (Pooled standard error =1532 cpm; for each line, starred points denote a significant difference from O PSPB (* P<0.1; ** P<0.01)).

The optimal concentration of mitogen may not have been reached. Without PSPB in the medium, incorporation of label was highest with the highest dose of mitogen, although this was very similar to the next lower dose. Regardless, stimulation of mitogenesis was greater with this mitogen than any other. In these highly responsive cells, PSPB did not have as dramatic an effect on inhibition of blastogenesis. Only at the 20 microgram dose was it inhibitory. The response with Con A as the mitogen is shown in FIG. 3.

The response at 5 micrograms of PSPB is interesting. The protein increased mitogenesis at the two lower doses of mitogen. As with the PHA response, when mitogenesis was not maximal without PSPB, PSPB had a stimulatory effect until a higher dose was reached.

Figure 4:
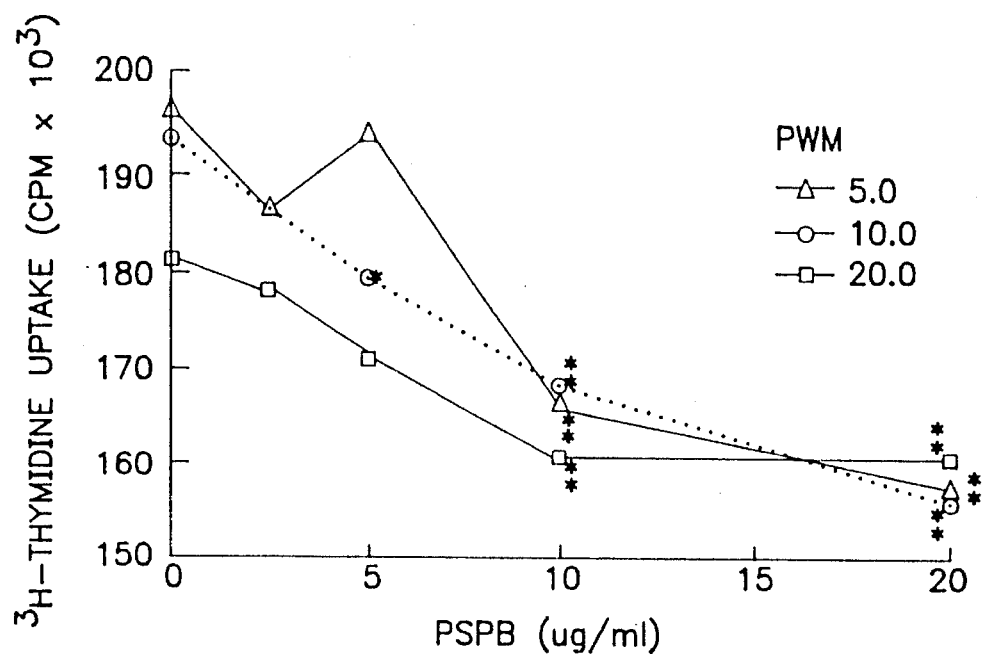
FIG. 4 shows PSPB suppression of pokeweed mitogen (PWM)-induced lymphocyte proliferation (Pooled standard error =1214 cpm; for each line, starred points denote a significant difference from O PSPB (* P<0.1; ** P<0.01)).

PWM stimulates both T and B lymphocytes. When no PSPB was added, optimal stimulation was reached with the lower two doses of mitogen. With the high dose, mitogenesis was obtained. Thus, optimum stimulation either was reached at 5 micrograms/ml or may have been reached even at lower doses had they been used. The response for the PWM mitogen is shown in FIG. 4.

PSPB reduced the incorporation of label. It was significantly less ($p<0.01$) at the two highest doses of PSPB. This reduction was not as dramatic as that seen for the PHA mitogen but was greater than that for Con A.

PSPB, a placental protein of the cow, in suppression of the mitogenic response of lymphocytes was shown to have immunosuppressive traits. PSPB was shown to inhibit blastogenesis in response to mitogens known to stimulate T and B lymphocytes. Con A and PHA are both T cell mitogens. PSPB inhibited responses in both cases but the degree of inhibition was the greatest for PHA and least for Con A. PWM, on the other hand, is both a T and B cell stimulator and the response was intermediate to that of the other two mitogens. Therefore, it is not possible to determine whether PSPB preferentially affects one cell type over the other.

Dose of mitogen and dose of PSPB seemed important to the pattern of response. In one case (with PHA) the above optimum dose of mitogen resulted in greater mitogenesis when PSPB was added while the opposite occurred at lower mitogen doses. In another case (Con A) when mitogen dose gave less than optimum stimulation, low doses of PSPB resulted in more blastogenesis while high doses of PSPB suppressed it. PSPB may find use in maintenance of pregnancy, particularly that of a foreign embryo and in immune suppression for tissue transplantation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for immunosuppressing a non-human animal host, said method comprising:

administering to said animal host in an amount sufficient to immunosuppress said animal host a Pregnancy Specific Protein B characterized as (a) isolatable from conceptustissue, (b) capable of suppressing mitogen-induced blastogenesis in vitro and (c) cross reactive with antisera to Pregnancy Specific Protein B.

2. The method according to claim 1, wherein said animal host is ruminant.

3. The method according to claim 2, wherein said ruminant is a domestic ruminant.

4. The method according to claim 3, wherein said domestic ruminant is bovine.

5. The method according to claim 1, wherein said Pregnancy Specfic Protein B is isolated from conceptus tissue.

6. A method for immounosuppressing a non-human animal host, said method comprising:

administering to said animal host in an amount sufficient to immunosuppress said animal host a bovine pregnancy specific protein B in a pharmaceutically acceptable carrier, said protein B characterized as (a) isolated from canceptus tissue, (b) capable of suppressing mitogen-induced blastogenesis in vitro and (c) cross reactive with antisera to bovine pregnancy specific protein B.

* * * * *